United States Patent
Mirjalili et al.

(10) Patent No.: US 11,454,826 B2
(45) Date of Patent: Sep. 27, 2022

(54) CONTACT LENS-BASED EYE TRACKING USING MAGNETIC FIELDS

(71) Applicant: Tectus Corporation, Saratoga, CA (US)

(72) Inventors: Ramin Mirjalili, San Jose, CA (US); Joseph Czompo, San Jose, CA (US); Thomas Llewellyn Owens, Saratoga, CA (US); Michael West Wiemer, San Jose, CA (US)

(73) Assignee: Tectus Corporation, Saratoga, CA (US)

( * ) Notice: Subject to any disclaimer, the term of this patent is extended or adjusted under 35 U.S.C. 154(b) by 394 days.

(21) Appl. No.: 16/839,066

(22) Filed: Apr. 2, 2020

(65) Prior Publication Data

US 2021/0311328 A1 Oct. 7, 2021

(51) Int. Cl.
*G02C 7/04* (2006.01)
*G06F 3/01* (2006.01)
*A61B 3/113* (2006.01)

(52) U.S. Cl.
CPC .............. *G02C 7/049* (2013.01); *A61B 3/113* (2013.01); *G02C 7/048* (2013.01); *G06F 3/013* (2013.01); *G02C 2200/02* (2013.01)

(58) Field of Classification Search
CPC .... G02C 7/049; G02C 7/048; G02C 2200/02; G02C 11/10; G02C 7/04; A61B 3/113; G06F 3/013; G06F 3/011; G06F 3/0346
See application file for complete search history.

(56) References Cited

U.S. PATENT DOCUMENTS

| 10,353,219 B1* | 7/2019 | Hannaford | ........... | H04N 13/366 |
| 2018/0149884 A1* | 5/2018 | Miller | .................. | H04B 5/0037 |
| 2020/0026097 A1* | 1/2020 | Pinel | .................. | G05B 13/0265 |

OTHER PUBLICATIONS

Mao et al., "A double-helix and cross-patterned solenoid used as a wirelessly powered receiver for medical implants", AIP Advances, v8, 0566603 (2018), 6 pages.

Nixon et al., "The effects of metals and interfering fields on electromagnetic trackers", Presence, v7, p. 204 (1998).

(Continued)

*Primary Examiner* — Darryl J Collins
*Assistant Examiner* — Matthew Y Lee
(74) *Attorney, Agent, or Firm* — Fenwick & West LLP (57) ABSTRACT

An augmented reality system determines the position and orientation of an eye. The system includes an electronic contact lens that projects images onto a user's retina. The contact lens includes magnetic sensors. The magnetic sensors detect magnetic fields along one axis, or more than one axis, depending on their configuration. The sensors may be a conductive coil, a solenoid, or a tunneling magnetoresistance device. The sensors detect magnetic fields generated by magnetic sources. The magnetic sources may be collocated, or non-collocated, on a wearable device, a device in the environment, or a secondary electronic device. The sources may have different orientations such that they produce magnetic fields along different axes, and the sensors are configured to independently detect the magnetic fields. The system determines the pose of the eye using a combination of the measurements, and the position and orientation of the sensors and sources.

21 Claims, 12 Drawing Sheets

(56) References Cited

OTHER PUBLICATIONS

Paperno et al., A New Method for Magnetic Position and Orientation Tracking, IEEE Transactions on Magnetics, vol. 37, No. 4, Jul. 2001, pp. 1938-1940.
Plotkin et al., Magnetic Eye Tracking: A New Approach Employing a Planar Transmitter, IEEE Transactions on Biomedical Engineering, vol. 57, No. 5, p. 1209-1215, May 2010.
Raab et al., Magnetic position and orientation tracking, IEEE Transactions on Aerospace and Electronic Systems, v AES-15, p. 709-718 (1979).
Robinson, A Method of Measuring Eye Movement Using a Scieral Search Coil in a Magnetic Field, IEEE Transactions on Bio-Medical Electronics, p. 137 (1963).

\* cited by examiner

CONTACT LENS-BASED EYE TRACKING USING MAGNETIC FIELDS

BACKGROUND

1. Technical Field

This disclosure relates generally to tracking methods for eye-mounted displays.

2. Description of Related Art

In one type of eye-mounted display, a tiny projector (referred to as a femtoprojector for convenience) is mounted inside a contact lens. A typical femtoprojector is no larger than about one or two millimeters in any dimension in order to fit inside the contact lens. The femtoprojector produces images and projects those images onto the user's retina. If the external environment is also visible, the projected images will be overlaid on the user's view of the external environment.

As the user's eye moves, the contact lens and femtoprojector also move—and the user's eye is always moving. For example, an eye may make involuntary saccadic motions, or voluntarily track a moving target using smooth pursuit motion. Whatever the circumstances, voluntary, or involuntary, eye motion occurs continuously as part of the human visual process. Because the femtoprojector also moves with the user's continuous eye motion, the location of where a projected image appears relative to the external environment constantly changes. However, eye-mounted displays capable of estimating the eye's orientation, position, or pose may use that estimate to give a projected image the appearance of remaining fixed with respect to the external environment.

DETAILED DESCRIPTION OF THE PREFERRED EMBODIMENTS

An augmented reality system adds computer-generated information to a person's view of the world around them. One example of an augmented reality system includes a contact lens mounted on a user's eye and an auxiliary device (e.g., a necklace). The contact lens includes small projectors that project information onto the user's retina so that the projected images are overlaid on their view of the world around them. The auxiliary device provides the contact lens with information for projecting onto the retina and, in some configurations, power for powering the projector and other components in the contact lens.

In order to project information onto the retina such that it appears at the correct location in the user's field of view, the augmented reality system may determine a pose of the eye. The pose of the eye includes both its position and its orientation. The position is the spatial position of the eye (e.g., x,y,z coordinates). It may be measured relative to the auxiliary device, the outside world, or other frame of reference. The orientation of the eye may be expressed in angular coordinates (e.g., $\theta_x$, $\theta_y$, $\theta_z$ coordinates) or quaternions. It may be measured relative to the eye socket, the auxiliary device, the outside world, or other frame of reference. Augmented reality is just one example application. Eye tracking can be used for many other applications.

One approach to eye tracking uses magnetic tracking techniques. To illustrate, an auxiliary device includes magnetic sources that generate non-spatially-uniform magnetic fields, and the contact lens includes magnetic sensors that measure magnetic fields. The magnetic fields may be constant, or vary in time, depending on the configuration of the system. The magnetic field measurements are different depending on the pose of the eye and, accordingly, the system can determine the pose of the eye based on the measurements.

There are several ways to implement magnetic sources and magnetic sensors to determine the pose of the eye. In one example implementation, the system includes two magnetic sensors and two magnetic sources. The magnetic sensors are non-collocated coils of wire around the perimeter of the contact lens that each measure a magnetic field along one axis. The magnetic sources are solenoids collocated on a collar-style necklace worn about a user's neck. The sources generate time-varying, spatially non-uniform, magnetic fields. Other implementations are possible, some of which are described herein. In some embodiments, the system includes a combination of four or more magnetic sources and magnetic sensors.

In some implementations, the system employs more complex methodologies when determining the pose of the eye. For example, the magnetic fields generated by the magnetic sources may be multiplexed. The magnetic sensors measure the multiplexed fields, and the system demultiplexes the measurements to determine the pose of the eye. In other examples, the system estimates the pose of the eye based on prior estimates of the pose, or adaptive filtering techniques such as Kalman filtering.

Figure 1A:
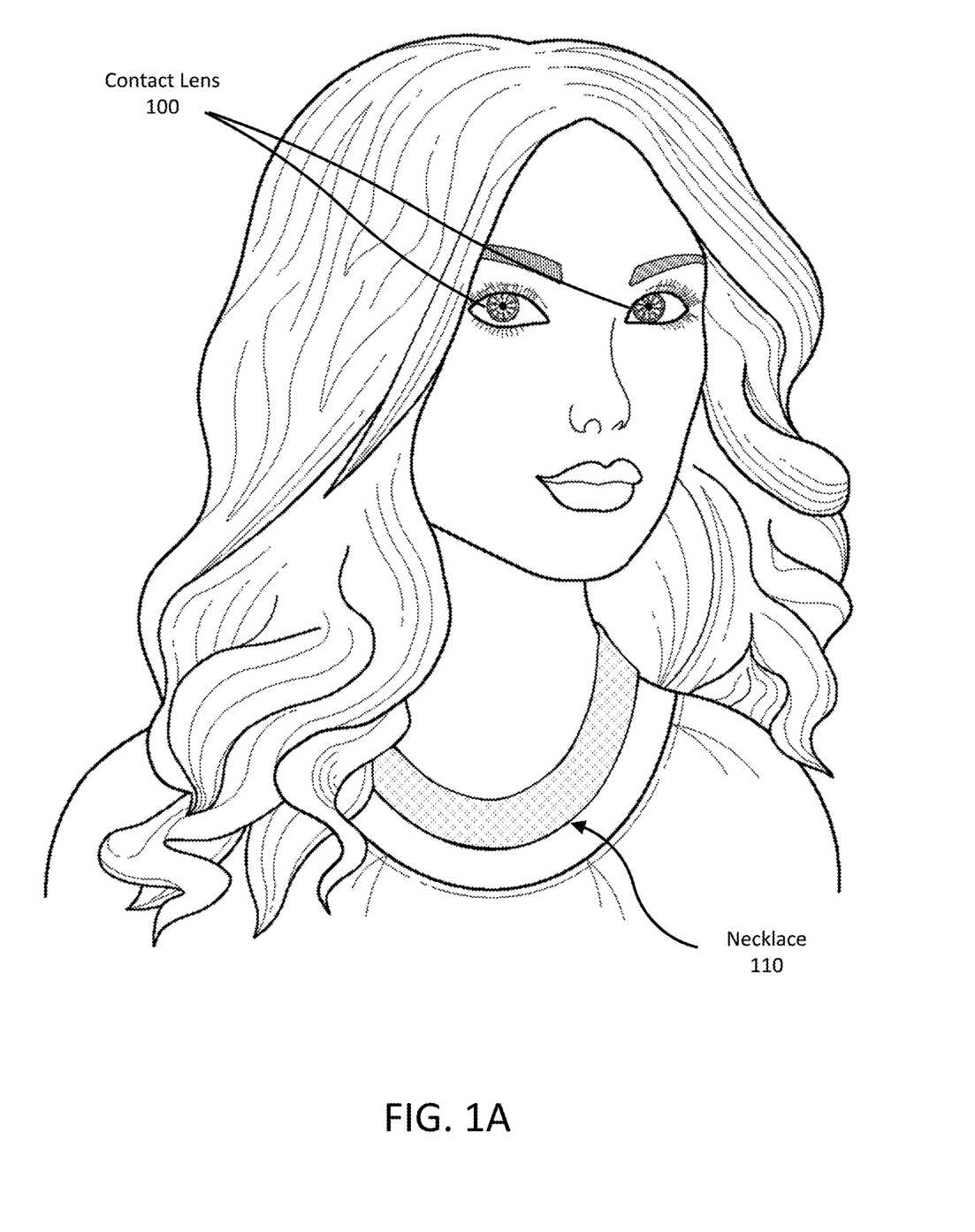
FIG. 1A shows a user wearing a display mounted in a scleral contact lens.
Figure 1B:
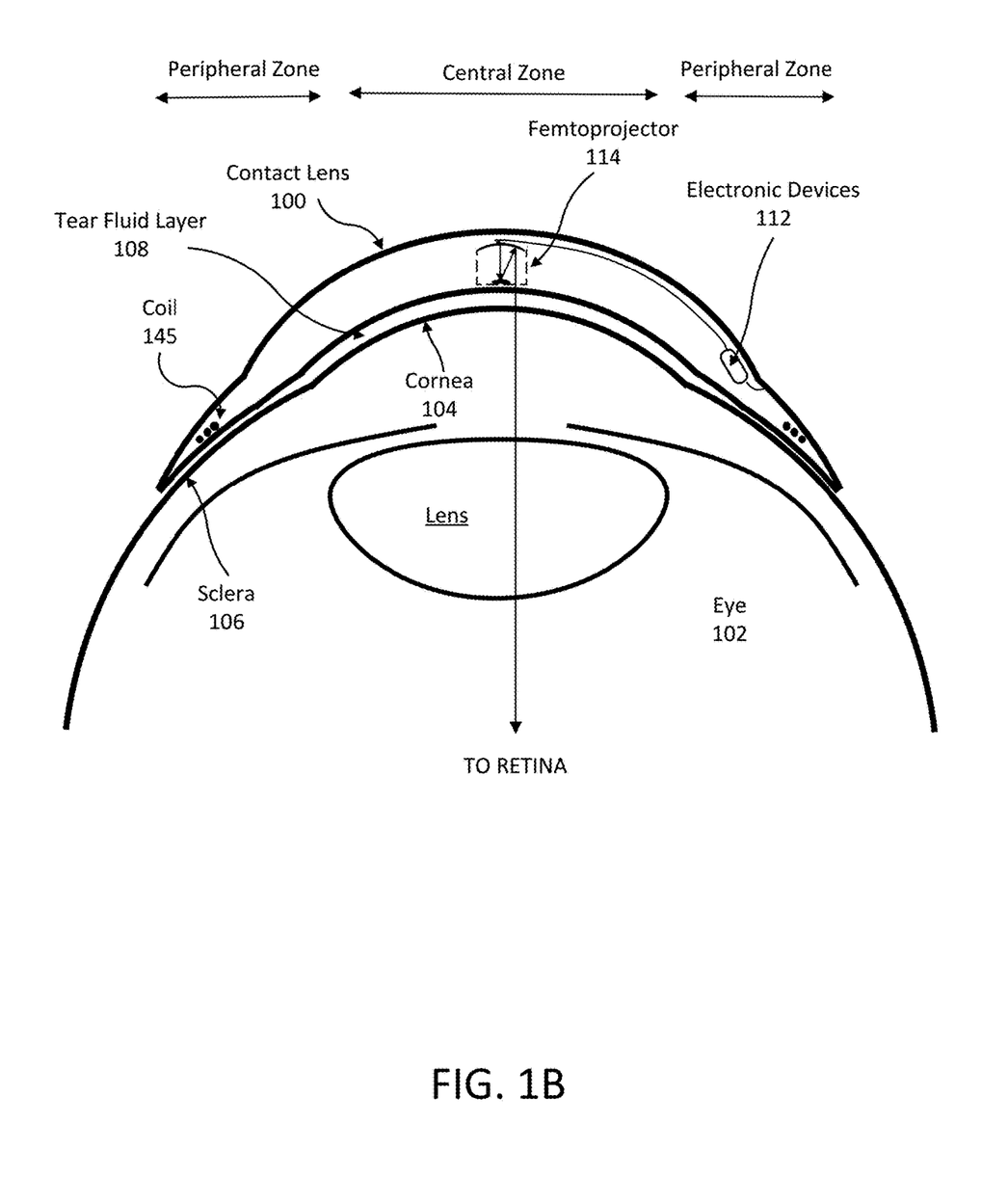
FIG. 1B shows a cross sectional view of the scleral contact lens mounted on the user's eye.

Further details for eye tracking methods are provided using an example of an electronic contact lens that includes small projectors that project images onto the user's retina. FIG. 1A shows a user wearing a display mounted in a scleral contact lens 100. In this example, the user is wearing an external device (e.g., necklace 110) that may be used to communicate with the contact lens 100 and/or provide the contact lens power. FIG. 1B shows a cross sectional view of the scleral contact lens 100 mounted on the user's eye. Scleral contact lenses are designed to not move around on the wearer's eye. The eye 102 includes a cornea 104 and a sclera 106. The scleral contact lens 100 is supported by the sclera 106 and vaults over the cornea 104. A tear fluid layer 108 may be formed between the contact lens 100 and the cornea 104. Oxygen permeates through the contact lens 100 to the cornea 104.

The contact lens 100 contains payload(s). For example, the payload(s) may include electronics, including electronics that require a power source such as a battery or a coil that is inductively powered. In the example of FIG. 1, the payloads include a small projector that projects images onto the user's retina (referred to as a femtoprojector 114), and the corresponding electronics 112 to operate the femtoprojector. The femtoprojector 114 may include an LED frontplane with an LED array, an ASIC backplane with electronics that receives the data to drive the LED frontplane, and optics to project light from the LED array onto the retina. The femtoprojector 114 preferably fits into a 2 mm by 2 mm by 2 mm volume or even into a 1 mm by 1 mm by 1 mm volume.

The femtoprojector 114 is positioned over the cornea since it projects images onto the retina. The electronics 112 may be positioned away from the cornea, as shown in FIG. 1B. For convenience, the contact lens 100 is divided into a central zone and a peripheral zone. The central zone overlaps the cornea 104. The area outside the cornea is part of the peripheral zone. In FIG. 1B, the femtoprojector 114 is located within the central zone of the contact lens because it projects images into the user's eye, while the electronics 112 and a coil 145 are located in the peripheral zone. Because people have eyes of different sizes and shapes, for convenience, the central zone may be defined as the 10 mm diameter center area of the contact lens (i.e., within 5 mm radius of the central axis of the contact lens). The diameter of the boundary between the cornea and the sclera is typically 10-12.5 mm. Payload components that project light onto the retina typically will be located within the central zone due to the required optical path. Conversely, payload components that do not project light onto the retina or otherwise interact with the retina may be located on the edge of the central zone or outside the central zone so that they do not block light from reaching the retina.

Other examples of powered payloads include sensors, imagers, and eye tracking components such as accelerometers, gyroscopes and magnetometers. Payloads may also include passive devices, such as a coil or antenna for wireless power or data transmission, capacitors for energy storage, and passive optical structures (e.g., absorbing light baffles, beam-splitters, imaging optics). The contact lens 100 may also contain multiple femtoprojectors, each of which projects images onto the user's retina.

The contact lens 100 moves with the user's eye 102 as the user's eye rotates in its socket. Because the femtoprojectors are mounted in the contact lens 100, they also move with the user's eye and project to the same region of the retina. Some femtoprojector(s) may always project images to the fovea, and other femtoprojector(s) may always project images to more peripheral regions which have lower resolutions. As a result, different femtoprojectors may have different resolutions. The images from different femtoprojectors may be overlapping, to form a composite image on the user's retina.

Figure 2:
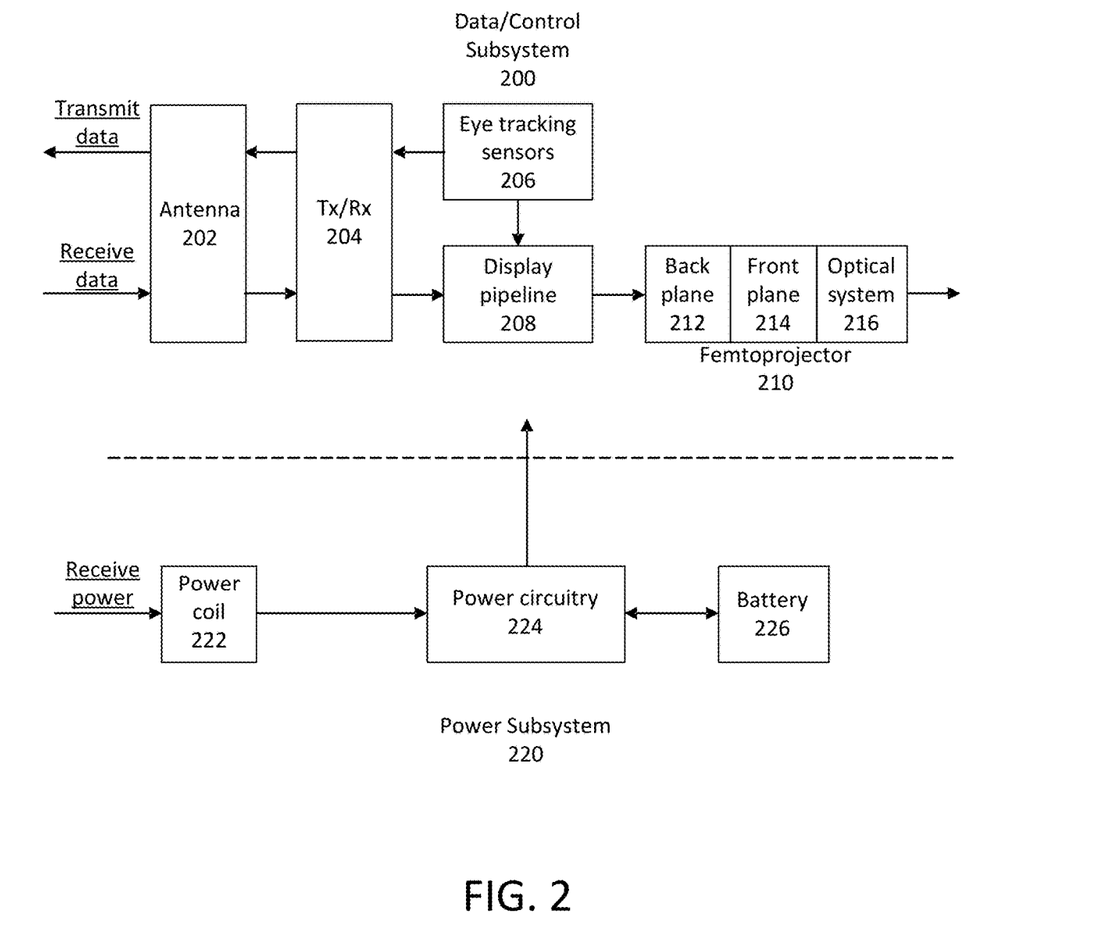
FIG. 2 is a functional block diagram of an eye-mounted display using a scleral contact lens.

FIG. 2 is a functional block diagram of an eye-mounted display using the scleral contact lens described above. The display can be divided into a data/control subsystem 200 and a power subsystem 220.

In this example, the receive path of the data/control subsystem 200 includes an antenna 202, transmission and receiver circuitry 204, a display pipeline 208, and a femtoprojector 210. Data from an external source is wirelessly transmitted to the display and received via the antenna 202. The receiver ("Rx") circuitry 204 performs functions for receiving the data, such as, for example, demodulation, noise filtering, and amplification. It also converts the received signals to digital form. The display pipeline 208 processes the digital signals for the femtoprojector 210. These functions may include decoding, and timing. The processing may also depend on other signals generated internally within the contact lens, such as, for example, eye tracking sensors 206, or ambient light sensing. Some example configurations for eye tracking sensors 206 are described in greater detail below. The femtoprojector 210 then projects the corresponding images onto the user's retina. In this example, the femtoprojector 210 includes a CMOS ASIC backplane 212, LED frontplane 214 and optical system 216.

The data/control subsystem 200 may also include a back channel. As illustrated, the back channel transmits data through transmitter circuitry ("Tx") 204 and antenna 202. For example, the contact lens may transmit eye tracking data, control data, and/or data about the status of the contact lens.

Batteries 226 provide power to the data/control subsystem 200 via power circuitry 224. The batteries may be inductively recharged via power coil 222. The power circuitry 224 may also condition the incoming power from the coil 222 (e.g., converting from AC to DC if needed).

In addition to the components shown in FIG. 2, the overall system may also include components that are outside the contact lens (i.e., off-lens). For example, eye tracking functions may be performed partly or entirely off-lens, as described below. The data pipeline may also be performed partially or entirely off-lens. Each of the arrows on the left-hand side of FIG. 2A also connects to an off-lens component. The power transmitter is off-lens, the source of image data and control data for the contact lens display is off-lens, and the receive side of the back channel is off-lens.

There are many ways to implement the different system functions. Some portions of the system may be entirely external to the user, while other portions may be worn by the user in the form of a headpiece or glasses. Components may also be worn on a belt, armband, wrist piece, necklace, or other types of objects as described herein. In other examples, the components may be in devices or structures near the user (e.g., the wall of a room, a tabletop data transmission system, etc.).

Figure 3:
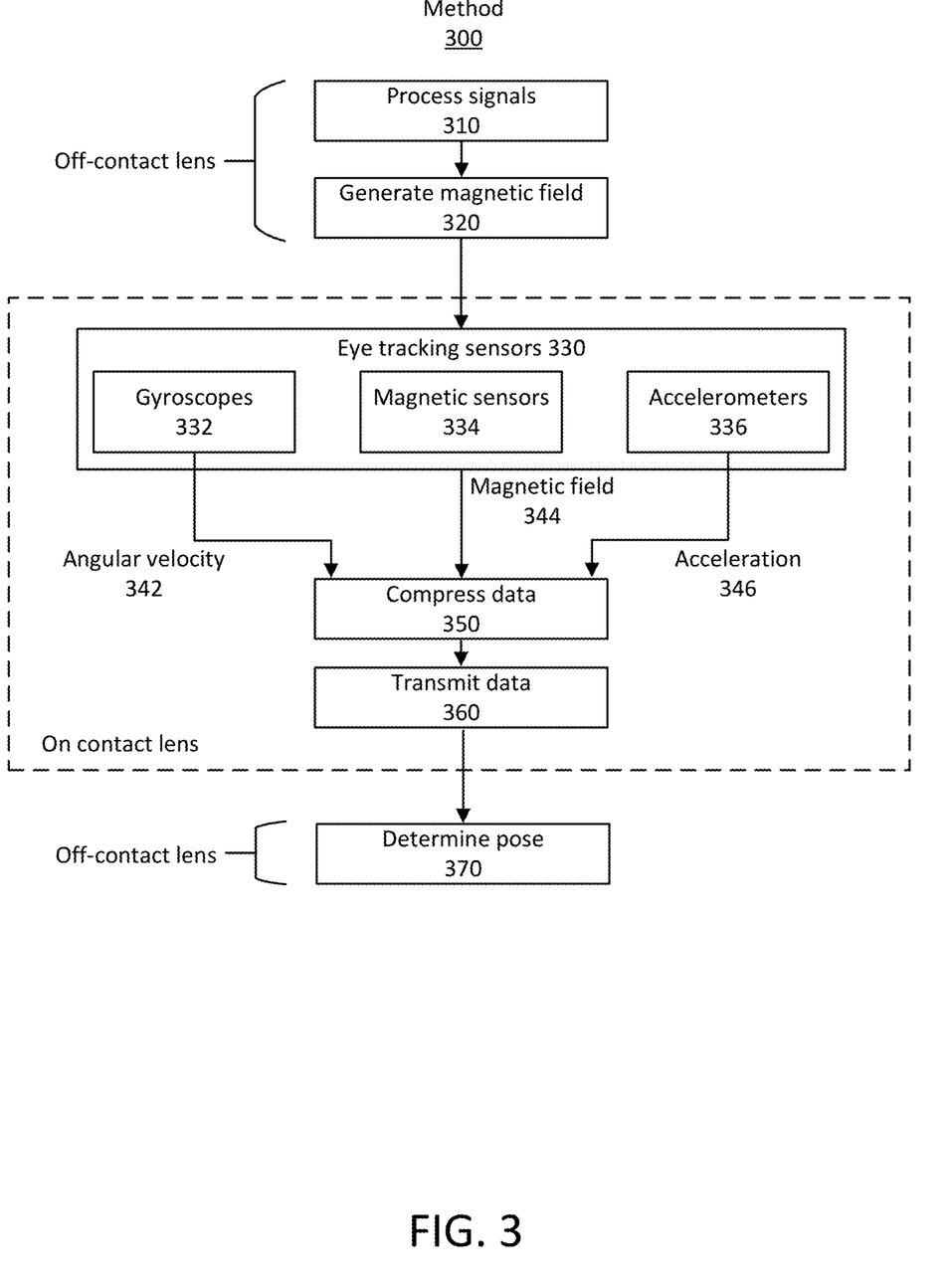
FIG. 3 shows a flow diagram of a method for determining the pose of the eye from measurements of a magnetic field generated by an external device.

The data/control subsystem 300 and an external device can be used to track the orientation and/or position of the eye wearing the contact lens. For example, FIG. 3 shows a flow diagram of a method 300 for determining the pose of the eye. Some aspects of the method 300 are performed off-contact lens, for example on an external device (e.g., a smartphone).

An external device generates and processes 310 signals for determining the pose of the eye. For example, generated DC signals are converted into AC signals suitable for driving a conductive coil. The AC signals are driven through a coil to generate 320 a time-varying magnetic field ("TVMF"). The device may also include more than one coil, and more than one TVMF may be simultaneously generated. In this case, the device may process 310 the signals such that each TVMF is independently distinguishable from one another. For example, device may time-multiplex the signals such that each TVMF is distinguishable by time-based characteristics. Frequency, phase, and code division multiplexing also possible. In some embodiments, the external device may generate a constant magnetic field.

Eye tracking sensors 330 on the contact lens sense information that may be used to determine the pose of the eye. To illustrate, in this example, one or more gyroscopes 332 measure angular velocity 342 at a known point(s) on the contact lens, one or more accelerometers 336 measure acceleration 346 at a known point(s) on the contact lens, and one or more magnetic sensors 334 measure the magnetic field(s) 344 at a known point(s) on the contact lens. The magnetic field(s) 344 may be an externally generated TVMF, or an externally generated constant magnetic field.

The measurements 342, 344, and 346 are taken on-lens (i.e., within the contact lens), because the corresponding sensors are on-lens. The contact lens may compress 350 the measurement data and transmit 360 measurement data off-lens using transmission circuitry and an antenna. The data may be transmitted to, for example, an external device.

Other types of pre-processing may also occur on-lens before transmission off-lens. Examples include smoothing, averaging and filtering of data; data cleaning and outlier checking of data; processing to generate a virtual inertial measurement unit (equivalent of accelerometers plus gyroscope); de-multiplexing and/or identifying magnetic field sources; and calculation of differential or differences over time, such as velocity change, position change, and orientation change. Other pre-processing steps are also possible An external device receives the measurements and determines 370 the position and/or orientation of the eye. The external device may be the same device that generated the TVMF, but could also be a different device. The device may also perform additional, or similar, pre-processing functions on the measurement data before determining the pose of the eye (e.g., de-multiplexing magnetic field measurements).

Various combinations of data from the sensors may be used determine 370 the pose of the eye. For example, acceleration 376 and magnetic field 374 measurements may be used to determine the pose, or angular velocity 372, acceleration 376, and magnetic field 374 measurements may be used. In some embodiments, only magnetic field 374 measurements are used to determine the pose. Additionally, Kalman filtering may be used to determine the pose using various combinations of measurements.

Figure 4A:
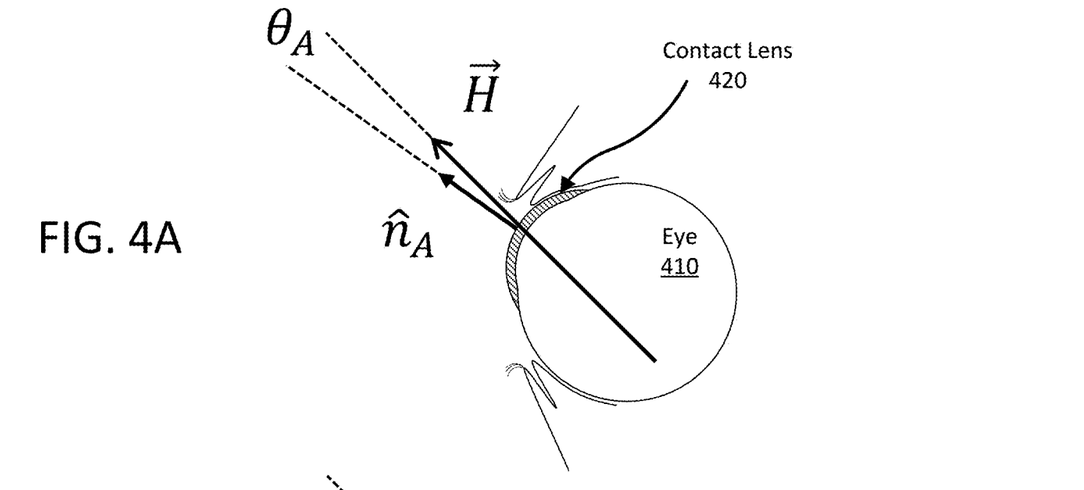
FIGS. 4A-4C show a series of drawings illustrating the eye moving in its socket, and showing how the system determines the pose of the eye using magnetic field measurements.
Figure 4B:
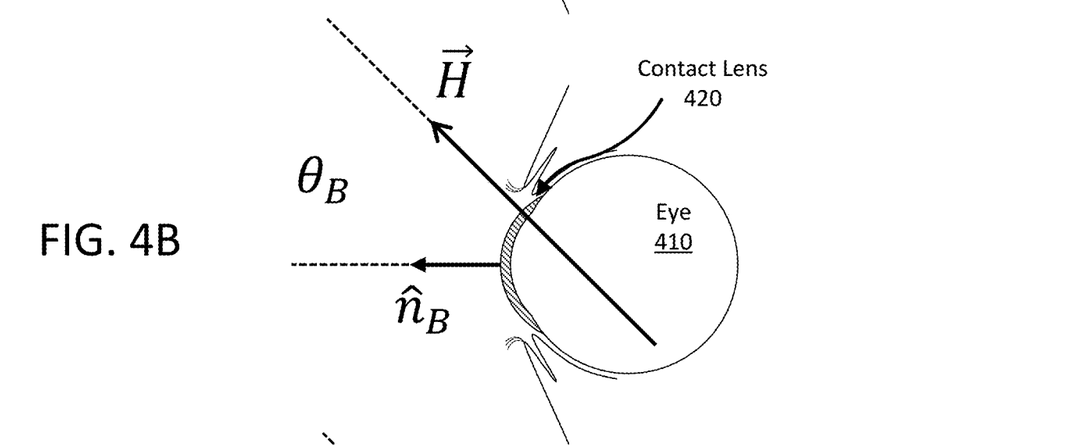
Figure 4C:
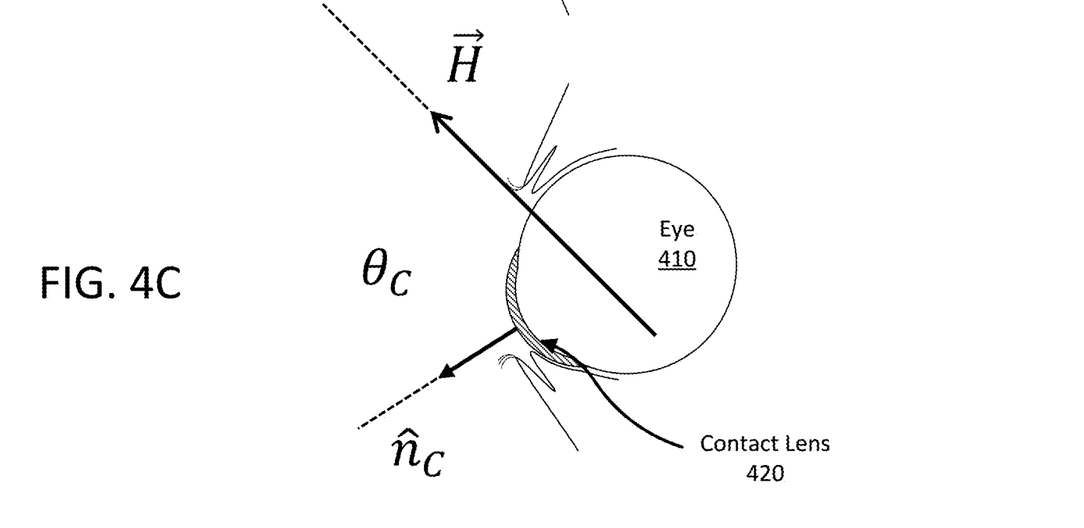

To provide context, FIGS. 4A-4C show a series of drawings illustrating the eye moving in its socket and showing how the system determines the pose of the eye using magnetic field measurements. Here, the system determines the orientation of the eye as it moves up and down, but other positions and orientations are also detectable.

In FIGS. 4A-4C, a magnetic source (not pictured) generates a magnetic field $\vec{H}$ at a constant orientation relative to the eye. $\vec{H}$ may be a spatially uniform magnetic field or a non-uniform magnetic field. $\vec{H}$ may vary in time or be constant in time. A contact lens 420 contains a magnetic sensor configured to measure the strength of magnetic fields in one direction. The user is gazing in a direction $\hat{n}$, and the magnetic sensor measures the strength of the magnetic field component in that direction. Here, as the direction of the user's gaze changes, the magnetic sensor measures different strengths resulting from the magnetic field $\vec{H}$.

To illustrate, FIG. 4A shows the eye 410 looking upwards. The direction of magnetic field $\vec{H}$ and direction of the user's gaze $\hat{n}_A$ are separated by an angle $\theta_A$. Because $\hat{n}_A$ and $\vec{H}$ are nearly parallel, the component $\vec{H}_A$ of magnetic field measured by the magnetic sensor is near maximum. In FIG. 4B, the user rotates their eye and turns their gaze forwards. At this point, the direction of magnetic field $\vec{H}$ and direction of the user's gaze $\vec{H}_B$ are now separated by an angle $\theta_B$. Because $\hat{n}_B$ and $\vec{H}$ are no longer nearly parallel, the component $\vec{H}_B$ measured by the magnetic sensor is decreased. Finally, in FIG. 4C, the user further rotates their eye and turns their gaze downwards. Now the direction of magnetic field $\vec{H}$ and direction of the user's gaze $\hat{n}_C$ are separated by an angle $\theta_C$ which is almost ninety degrees. Because $\hat{n}_C$ and $\vec{H}$ are nearly perpendicular, the component $\vec{H}_C$ measured by the magnetic sensor is near minimum.

The magnetic field strength $H_A$ measured in FIG. 4A is highest because $\hat{n}_A$ is nearly parallel to $\vec{H}$, while the magnetic field strength $H_C$ measured in FIG. 4C is lowest because $\hat{n}_C$ is nearly perpendicular to $\vec{H}$. A range of other magnetic field strengths are possible depending on the rotation of the eye in the socket.

The system can determine the pose of the eye based on the measured magnetic field strength. For example, the system determines the orientation of the eye is $\hat{n}_A$ when the magnetic sensor measures strength $H_A$, $\hat{n}_B$ when the magnetic sensor measures strength $H_B$, etc. To do so, the system may associate certain measurements of $\vec{H}$ with specific orientations $\hat{n}$.

Similarly, the system may determine the pose based on the measurements and the known position and/or orientation of the eye. For example, the system may store the forward-looking orientation of the eye $\hat{n}_B$ and its corresponding measurement $H_B$, and the system may determine subsequent orientations based on that information. If sensors measure a field greater than $H_B$, the eye is looking upwards, while a measurement less than $H_B$ indicates the eye is looking downwards. The magnitude of change in the measurement can indicate the degree at which the eye has changed orientation.

The system can also determine the pose based on the orientation of the magnetic source, and the distance between the magnetic source and the magnetic sensor. To illustrate, when the magnetic field measurement is highest, the system determines the contact lens is oriented approximately parallel to the magnetic field because the orientation of the magnetic source, and the distance between the magnetic source and magnetic source are known.

The contact lens can also sense magnetic fields in directions other than that of the user's gaze. To illustrate, a contact lens includes three single-axis magnetic fields and is in the presence of a magnetic field $\vec{H}$. The sensors are oriented such that the sensing axes are orthonormal (e.g., the x, y, and, z axes, respectively). The sensors may be in approximately the same position (e.g., collocated), or in different positions (e.g., non-collocated) within the contact lens.

When the contact lens is oriented such that the x, y, or z axis is parallel to $\vec{H}$, only the corresponding magnetic sensor will sense a significant component of the magnetic field. When the contact lens is oriented such that none of x, y, or z axes are parallel to $\vec{H}$, all the sensors measure some component of the magnetic field. In other words, as the eye rotates, magnetic sensors in the contact lens generate different measurements based on their relative orientation to $\vec{H}$. The system determines the pose of the eye based on the combination of measurements. For example, here, because each of the sensors sense along a specific axis, each of the measurements correspond to an x, y, or z component of the contact lens' position and/or orientation. The system uses the measured components of the contact lens to determine the pose of the eye.

The sensing directions of magnetic sensors in a contact lens need not be orthonormal. For example, a contact lens may include three differently oriented magnetic sensors sensing fields in axes corresponding to the $\hat{x}+\hat{y}$, $\hat{y}$, and $\hat{y}+\hat{z}$ directions, respectively, where $\hat{x}$, $\hat{y}$, and $\hat{z}$ represent a set of orthonormal unit vectors. The system may use the position and/or relative orientation of the magnetic sensors to determine the pose. For example, the system may decouple measurements representing $\hat{x}$, $\hat{y}$, and $\hat{z}$ directions to determine the eye's pose because the relative orientations between magnetic sensors and/or magnetic sources is known.

A contact lens may include magnetic sensors capable of measuring a magnetic field along more than one axis. For example, a single magnetic sensor may be configured to measure a magnetic field along two orthogonal axes (e.g., x and y) and provide those measurements to the system. Thus, a contact lens may include fewer magnetic sensors than total number of measurement axes. For example, a contact lens may include two magnetic sensors that sense a magnetic field along three axes, e.g., a first magnetic sensor that senses along the x and y axes, and a second magnetic sensor that senses along the z axis.

Various types of magnetic sensors may be included in a contact lens depending on its configuration. In a first example, a contact lens includes conductive coils acting as magnetic sensors. The conductive coils detect changes to a time-varying magnetic field passing through the coil (e.g., a time derivative) and generate a voltage corresponding to both the relative orientation between the magnetic field and the coil, and the magnitude of the magnetic field change. The system measures the generated voltage to determine the pose of the eye.

Figure 5A:
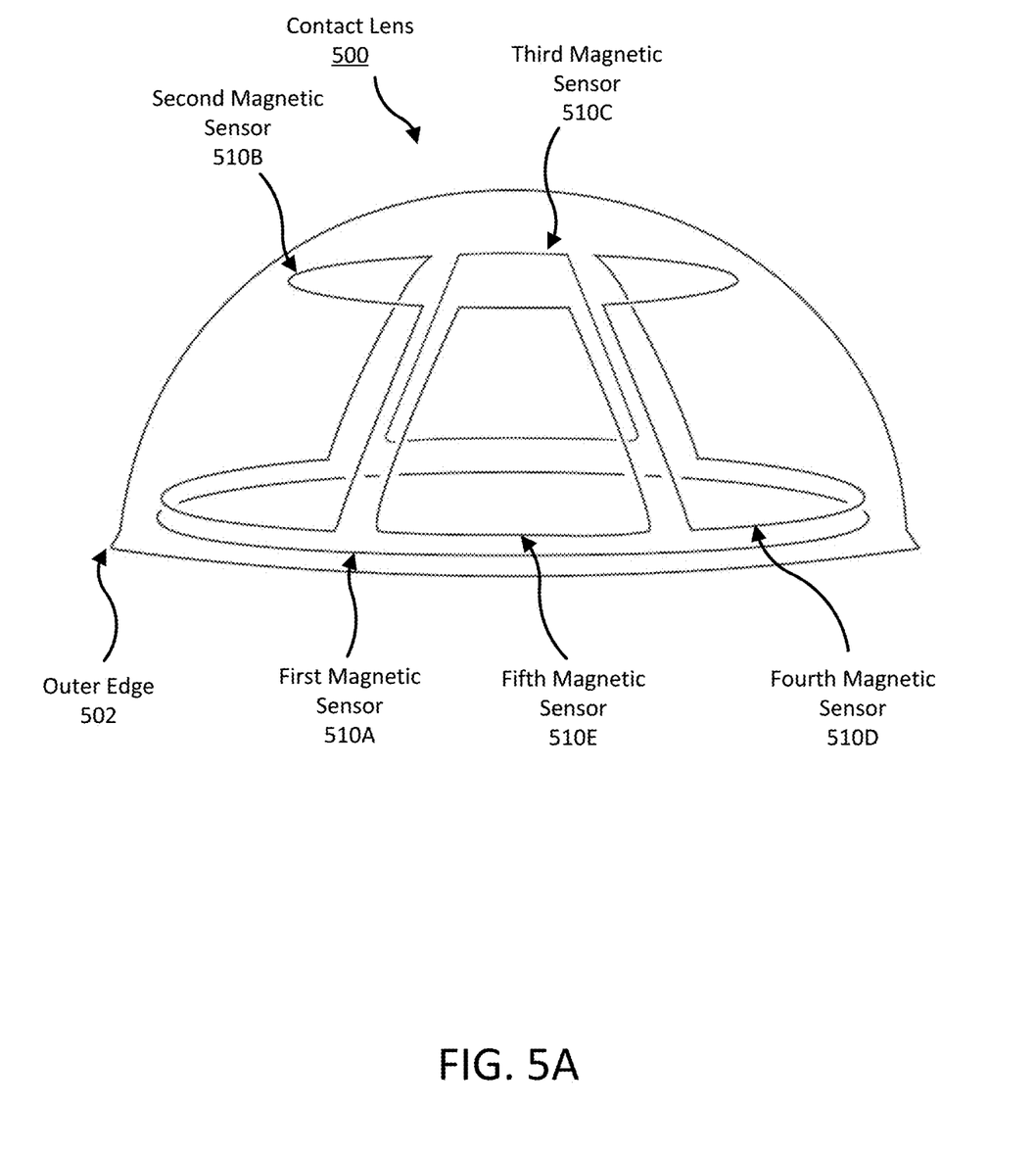
FIG. 5A-5B illustrate a contact lens including five conductive coil magnetic sensors.
Figure 5B:
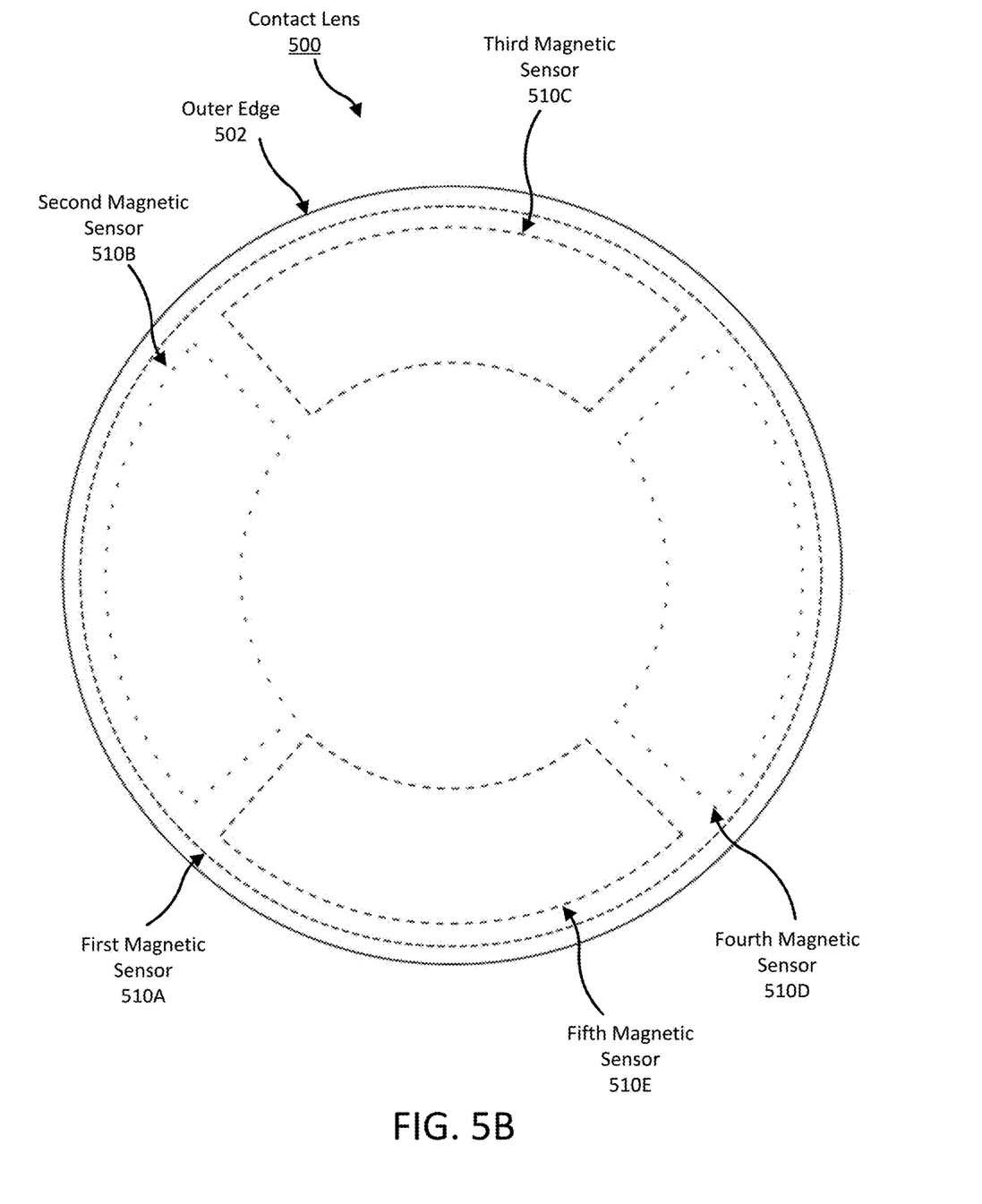

FIG. 5A shows a side view of a contact lens including five conductive coil magnetic sensors. FIG. 5B is a plan view of the contact lens 500. The first magnetic sensor 510A is near the bottom of the contact lens and is concentric with the outer edge 502. The second 510B, third 510C, fourth 510D, and fifth 510E magnetic sensors are shown within the sidewalls of the contact lens. Other numbers and orientations of conductive coil magnetic sensors are also possible. Some examples are demonstrated in U.S. patent application Ser. No. 16/035,640 titled "Eye-Mounted Displays Including Embedded Conductive Coils," which is hereby incorporated by reference in its entirety.

In a second example, a contact lens includes solenoids configured as magnetic sensors. Physical dimensions of the solenoid affect its sensing capabilities and may be implemented to improve sensor performance. For example, long thin solenoids have a higher quality factor Q than short fat solenoids. The solenoids measure changes in a time-varying magnetic field passing through the center of the solenoid and generate a voltage corresponding to both the relative orientation between the magnetic field and the solenoid, and the magnitude of the change. The system measures the generated voltage to determine the pose of the eye.

Figure 6A:
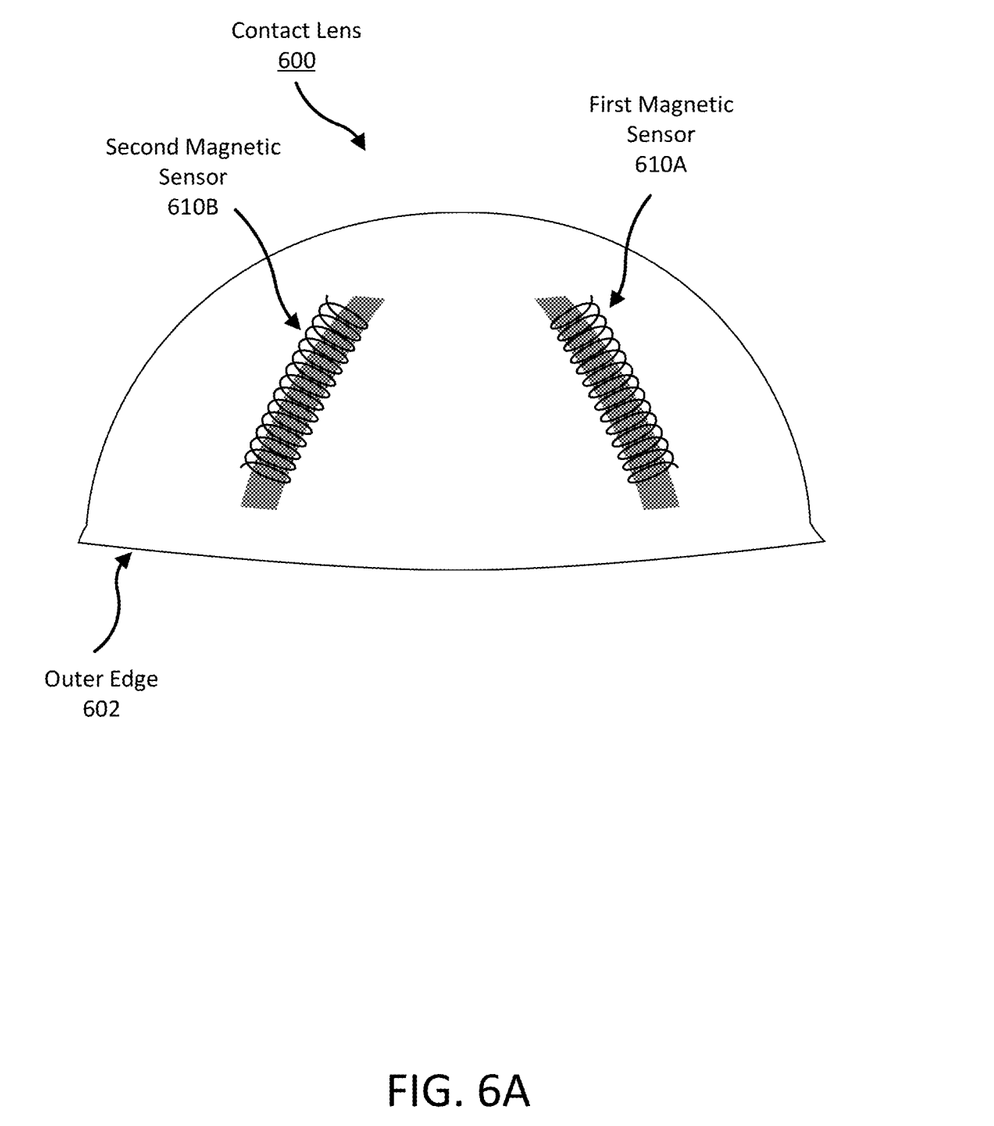
FIG. 6A-6B illustrate a contact lens including three solenoid magnetic sensors.
Figure 6B:
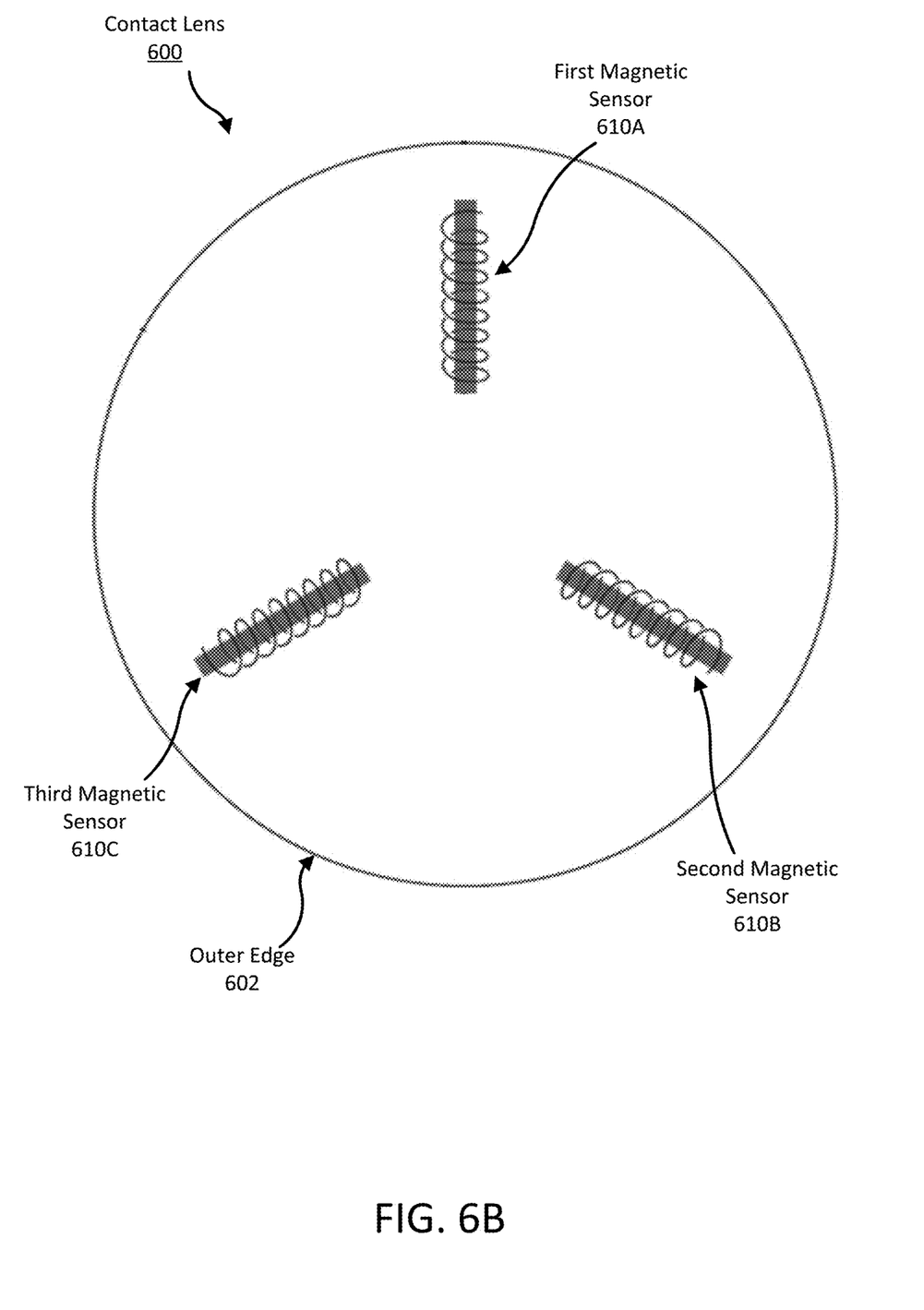

FIG. 6A shows a side view of a contact lens including three solenoid magnetic sensors. FIG. 6B is a plan view of the contact lens 600. The first magnetic sensor 610A and second magnetic sensor 610B are shown in the sidewalls of the contact lens 600. The third magnetic sensor 610C is not illustrated in FIG. 6A because it is on the opposite side of the contact lens 600. The plan view of FIG. 6B shows the third magnetic sensor 610C. The axes of the magnetic sensors 610A-C are directed from the outer edge 602 towards the center of the contact lens 600. The axes of the magnetic sensors may be straight, or they may curve to fit the contour of the contact lens. Other numbers and orientations of solenoid magnetic sensors are also possible. Some examples are demonstrated in U.S. patent application Ser. No. 16/200,039 titled "Eye-Mounted Displays Including Embedded Solenoids," which is hereby incorporated by reference in its entirety.

In a third example, a contact lens includes one or more TMR (tunneling magnetoresistance) devices that act as magnetic sensors. Physical properties of a TMR device (e.g., direction of magnetization) change based on the relative orientation between the device and a constant magnetic field, and the contact lens measures and quantifies those changes. The changes may be measured using a voltage differential, resistance value, or current change, depending on the type of TMR device and configuration of the contact lens. The system determines the pose of the eye based on the measurements.

Contact lenses can also include a combination of magnetic sensor types. For example, a contact lens may include (i) a single TMR magnetic sensors that senses single axis, a (ii) conductive coil magnetic sensors that senses a single axis, and (iii) two solenoid magnetic sensor that senses multiple axes. Other combinations of magnetic sensor types are also possible.

The magnetic sensors can sense magnetic fields generated by more than one magnetic source; for example, by one, two, three, or four magnetic sources. The magnetic sources may be coupled to, or located in, different objects. Some example objects include as a personal auxiliary electronic device such as a smartphone or tablet computer, or a wearable object such as a hat, shirt, or necklace. In some cases, the objects are within the user's environment. Some example environmental objects include a wall in a room, or the roof of a car.

The magnetic sources may each have a different orientation and produce magnetic fields with different strengths and/or along different axes. For example, a system can include three magnetic sources that produce three different magnetic fields $\vec{H}_1$, $\vec{H}_2$, and $\vec{H}_3$, respectively. Magnetic sensors in the contact lens sense the different fields and determine the pose of the eye based on their measurements.

The magnetic sensors sense the aggregate magnetic field created by the sum of the individual fields, i.e., the magnetic sensors measure $\vec{H}_T$ where $\vec{H}_T=\vec{H}_1+\vec{H}_2+\vec{H}_3$. However, the magnetic sources may multiplex the different magnetic fields using time, frequency, or code division multiplexing techniques, so that the system may demultiplex the corresponding measurements. For example, three magnetic sources are oriented such their multiplexed magnetic fields $\vec{H}_1$, $\vec{H}_2$, and $\vec{H}_3$ are orthogonal to one another at the contact lens. A single magnetic sensor measures each magnetic field independently according to the multiplexing scheme. The system assigns each of the demultiplexed measurements to the appropriate magnetic source and determines the pose of the eye. For example, the system determines the eye's orientation using the measurements because $\vec{H}_1$, $\vec{H}_2$, and $\vec{H}_3$ are approximately orthogonal and the relative orientation between the contact lens and the magnetic sensors is known. Other orientations and methodologies are also possible.

Magnetic sources may be collocated, or non-collocated. Collocated magnetic sources are at approximately the same position, while non-collocated sources are at different positions. For example, a necklace may include two collocated sources in a pendant, or a t-shirt may include two non-collocated sources on opposite sleeves. In another example, a boardroom table may include three collocated sources in the center of a table, while a wall of a room may include four non-collocated sources in different corners.

Figure 7A:
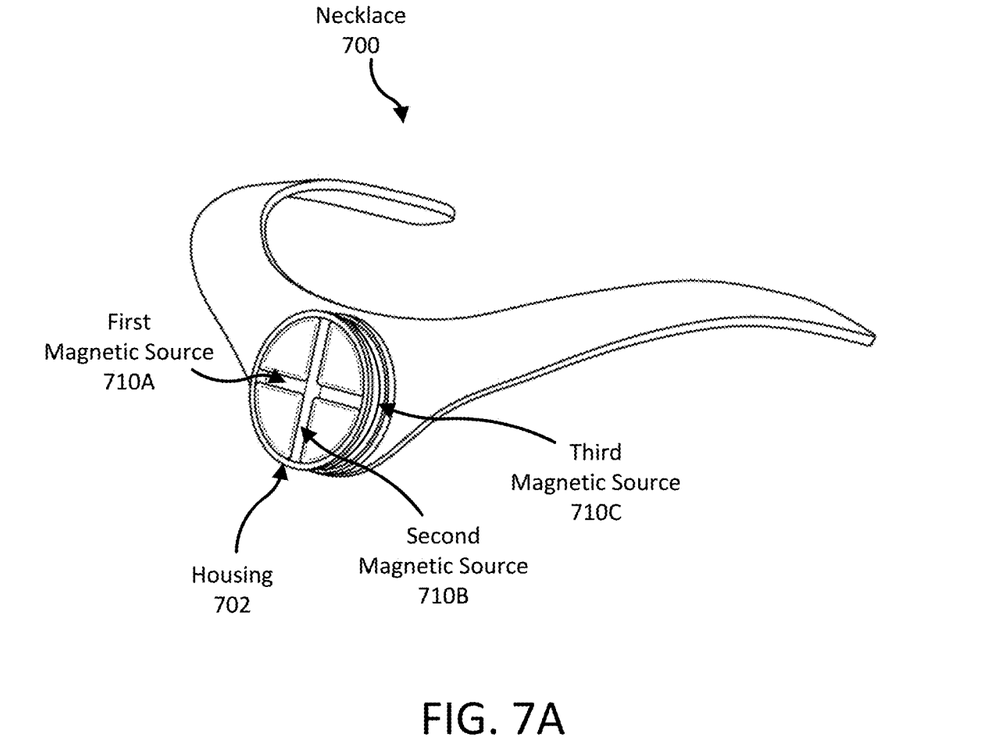
FIG. 7A shows a perspective view of a collar style necklace including three collocated magnetic sources.
Figure 7B:
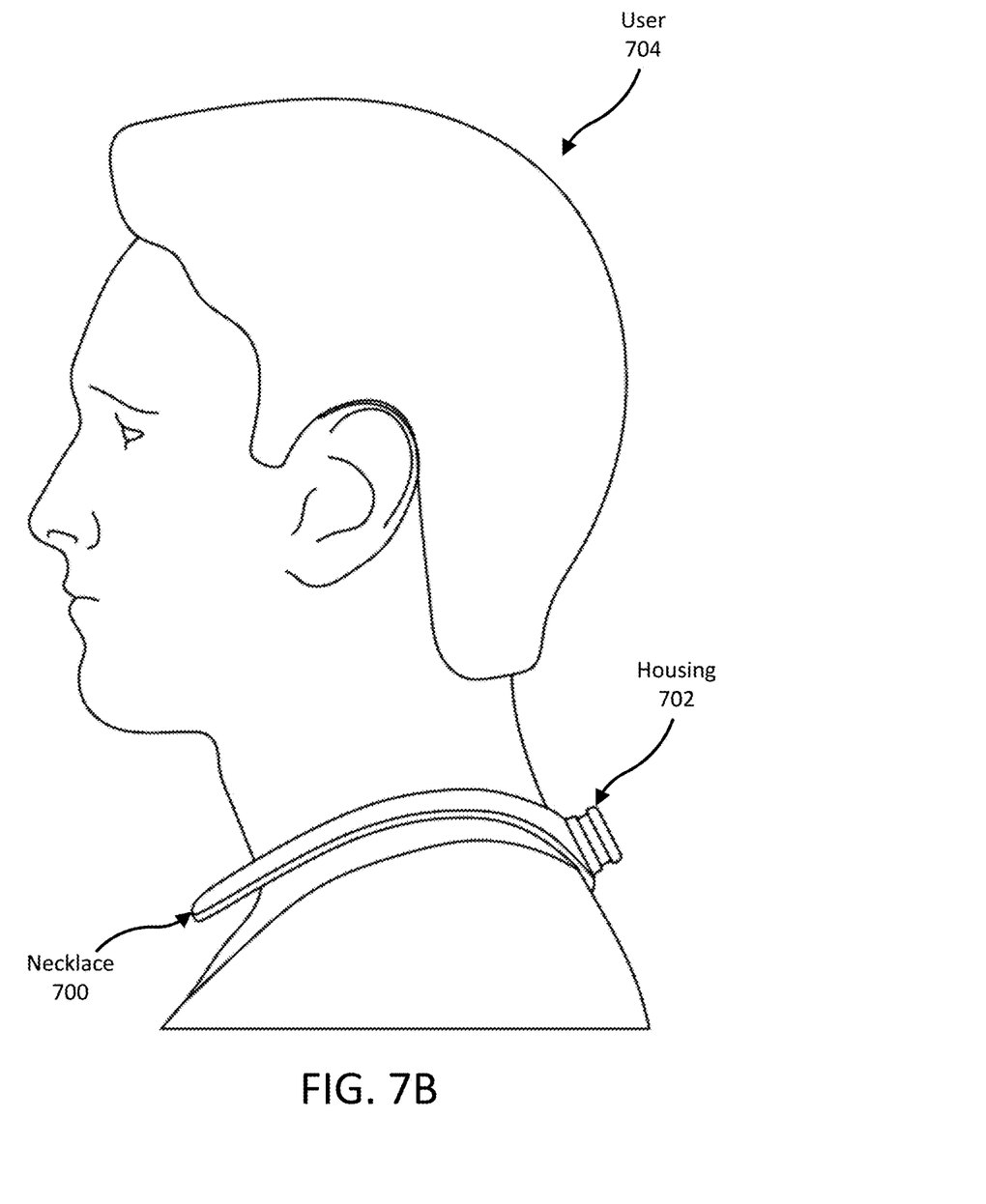
FIG. 7B shows a side view of a user wearing the necklace of FIG. 7A.

To illustrate, FIG. 7A shows a perspective view of a collar style necklace including three collocated magnetic sources. FIG. 7B shows a side view of a user wearing the necklace. The necklace 700 includes a housing 702 shaped as a planar medallion, but the housing 702 could take other shapes. When worn by the user 704, the housing 702 sits on his upper back, but could be in another position, such as above his sternum, or atop his shoulder.

The first and second magnetic sources 710A-B have different orientations and are collocated on the plane of the medallion. The third magnetic source 710C is collocated with the first and second sources but encircles them on the plane of the medallion. The first and second magnetic sources 710A-B are solenoids, while the third magnetic source 710C is a conductive coil. Each of the magnetic sources generate a magnetic field along a different axis. That is, the first, second, and third sources 710A-C generate a magnetic field along a first, second, and third axes, respectively. Here, the first and second axes are orthogonal, but could be in some other non-parallel orientation. The third axis is orthogonal to both the first and second axes but need not be so.

Figure 8:
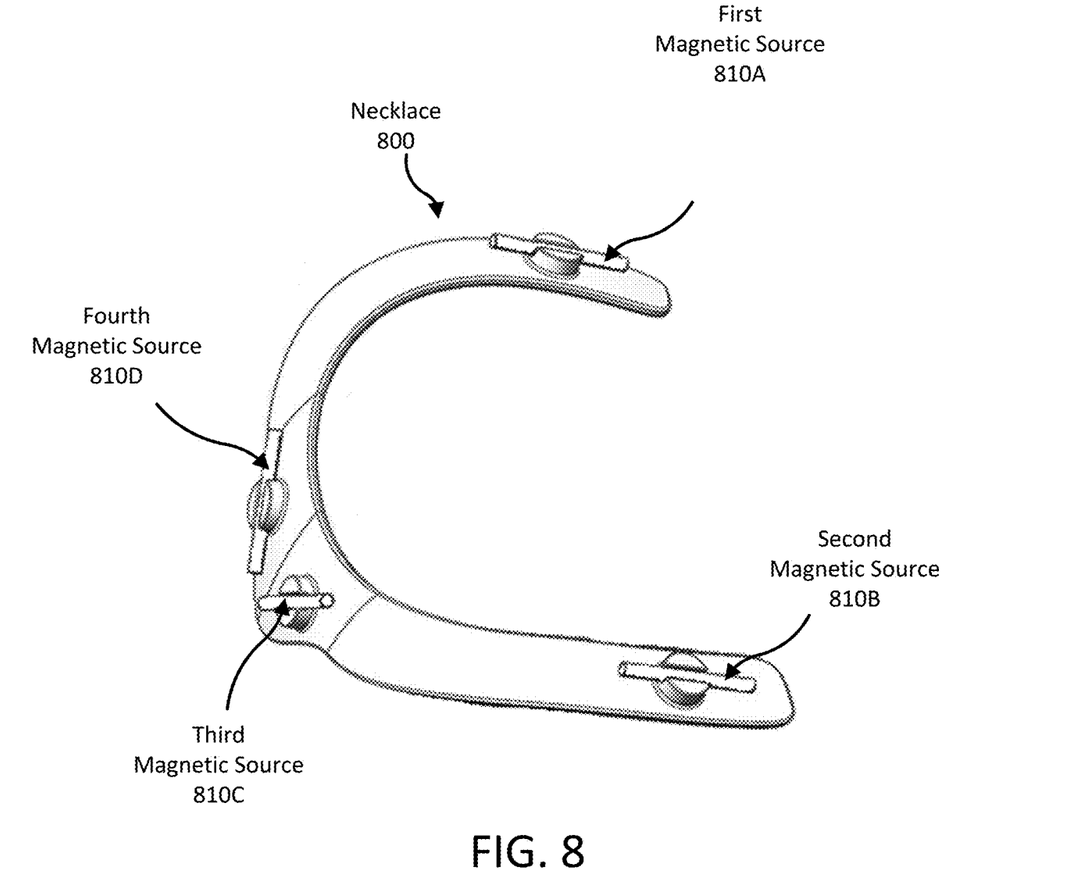
FIG. 8 shows a perspective view of a collar style necklace including four non-collocated magnetic sources.

As another example, FIG. 8 shows a perspective view of a collar style necklace including four non-collocated magnetic sources. Each of the magnetic sources is a solenoid but could be a different type of magnetic source. When the necklace 800 is worn, the first and second magnetic sources 810A-B are located on opposite shoulders, and the third and fourth magnetic sources 810C-D are at different locations on the upper back. The first and second magnetic sources 810A-B have similar orientations and produce magnetic fields along approximately parallel axes. The third and fourth magnetic sources 810C-D have different orientations and produce magnetic fields along different axes, and those axes are different than the axes of the first and second magnetic sources 810A-B.

Described above are a multitude of configurations for an AR system employing magnetic sources external to a contact lens, and magnetic sensors internal the contact lens to determine the pose of a wearer's eye. The disclosed embodiments are not exclusionary, and an AR system may include various configurations of both magnetic sensors and magnetic sources. For example, the system may include a contact lens with five conductive coil single-axis magnetic sensors, and three collocated magnetic sources on a necklace. As a second example, the system may include a contact lens with one TMR three-axis magnetic sensors, and four non-collocated magnetic sensors on a necklace. Generally, the combined number of sensors and sources is at least four such that the system can accurately determine the pose of the eye. That is, the system may have at least one sensor and three sources, two sensors and two sources, or three sensors and one source.

Additionally, the system may employ any combination of the techniques disclosed herein to determine the pose of the eye using the various types information within the AR system. For example, the system may determine the pose using any of (i) magnetic sensor measurements, (ii) other sensor measurements, (iii) a known position of the contact lens, (iv) a known orientation of the contact lens, (v) a known relative orientation between magnetic sources and magnetic sensors, and (vi) previous pose information. For example, the system may estimate the pose of the eye in a particular quadrant of a sphere based on measurements from the contact lens, and resolve symmetric quadrant ambiguity based on the position and orientation of the magnetic sources. However, the position and orientation of the sources may not be necessary if there is sufficient other information (e.g., a previous pose of the eye). In another example, the system may determine the pose by employing sensor fusion and a Kalman filter.

Although the detailed description contains many specifics, these should not be construed as limiting the scope of the invention but merely as illustrating different examples. It should be appreciated that the scope of the disclosure includes other embodiments not discussed in detail above. Various other modifications, changes and variations which will be apparent to those skilled in the art may be made in the arrangement, operation and details of the method and apparatus disclosed herein without departing from the spirit and scope as defined in the appended claims. Therefore, the scope of the invention should be determined by the appended claims and their legal equivalents.

What is claimed is:

1. An eye tracking system comprising:
a contact lens containing one or more magnetic sensors within the contact lens, the one or more magnetic sensors including two magnetic sensors with different orientations;
one or more magnetic sources that generate non-spatially-uniform magnetic fields at the magnetic sensor(s); and
a processor that determines at least one of a position and an orientation of the eye based at least in part on measurements of the magnetic fields by the magnetic sensors.

2. The eye tracking system of claim 1, wherein the one or more magnetic sensors include three single-axis magnetic sensors with different orientations from one another.

3. The eye tracking system of claim 1, wherein the one or more magnetic sources include two collocated magnetic sources with different orientations.

4. The eye tracking system of claim 1, wherein the one or more magnetic sources include two non-collocated magnetic sources.

5. The eye tracking system of claim 1, wherein a combined number of the one or more magnetic sensors and the one or more magnetic sources is at least four.

6. The eye tracking system of claim 1, wherein the one or more magnetic sources include two single-axis magnetic sources with different orientations collocated in a planar medallion wearable by a user of the contact lens.

7. The eye tracking system of claim 1, wherein the one or more magnetic sources include three single-axis magnetic sources with different orientations collocated in a planar medallion wearable by a user of the contact lens.

8. The medallion of claim 7, wherein:
two of the three single-axis magnetic sources include ferrite-core wire coils with axes lying in a plane of the medallion but non-parallel to each other, and
a third of the three single-axis magnetic sources includes a wire coil that encircles the other two single-axis magnetic sources and has an axis orthogonal to the plane of the medallion.

9. The eye tracking system of claim 1, wherein the one or more magnetic sources include four non-collocated magnetic sources mounted on a collar of a collar necklace.

10. The eye tracking system of claim 1, wherein the one or more magnetic sources are mounted on a wearable device.

11. The eye tracking system of claim 1, wherein the one or more magnetic sources are located in an environment within which the user uses the contact lens but not on the user.

12. The eye tracking system of claim 1, wherein the one or more magnetic sensors measure a time derivative of the magnetic field.

13. The eye tracking system of claim 1, wherein the one or more magnetic sensors measure a strength of the magnetic field along one or more measurement axes.

14. The eye tracking system of claim 1, wherein one of the magnetic sensors is a tunneling magnetoresistance sensor.

15. The eye tracking system of claim 1, wherein the processer applies a Kalman filter to the magnetic field measurements to determine at least one of the position and the orientation of the eye.

16. The eye tracking system of claim 1, wherein the processor determines at least one of the position and the orientation of the eye by:
    determining at least one of the position and the orientation of the eye, subject to quadrant ambiguity, based at least in part on measurements of the magnetic fields by the magnetic sensors, and
    resolving the quadrant ambiguity based on a known position of the one or more magnetic sensors relative to the one or more magnetic sources.

17. The eye tracking system of claim 1, wherein the processor determines at least one of the position and the orientation of the eye without using a prior position or a prior orientation of the eye.

18. The eye tracking system of claim 1, further comprising:
    one or more accelerometers for measuring an acceleration of the contact lens, wherein the processor determines the at least one of the position and the orientation of the eye further based on measurements of the acceleration by the accelerometers.

19. The eye tracking system of claim 1, further comprising:
    one or more gyroscopes for measuring an angular velocity of the contact lens wherein the processor determines at least one of the position and the orientation of the eye further based on measurements of the angular velocity by the gyroscopes.

20. The eye tracking system of claim 1, wherein:
    the one or more magnetic sources includes at least two multiplexed magnetic sources,
    the processor demultiplexes measurements from the one or more magnetic sensors based on the multiplexing of the magnetic sensors, and
    the processor determines at least one of the position and the orientation of the eye using the demultiplexed measurements.

21. The eye tracking system of claim 1, wherein the one or more magnetic sensors are not collocated within the contact lens.

* * * * *